United States Patent [19]
Whatley et al.

[11] Patent Number: 5,925,594
[45] Date of Patent: Jul. 20, 1999

[54] METHOD TO OVERCOME THE ANTAGONISTIC INTERACTIONS OF HERBICIDES

[75] Inventors: Thomas Whatley, East Windsor, N.J.; Todd L. Frazier, Aurora, Colo.; Roger W. Krueger, Baldwin, Mo.

[73] Assignee: American Cyanamid Company, Madison, N.J.

[21] Appl. No.: 08/873,094

[22] Filed: Jun. 11, 1997

Related U.S. Application Data

[60] Provisional application No. 60/019,562, Jun. 11, 1996.

[51] Int. Cl.$^6$ .......................... A01N 25/32; A01N 43/50; A01N 37/10
[52] U.S. Cl. .............................. 504/105; 504/130
[58] Field of Search ...................... 504/105, 130

[56] References Cited

U.S. PATENT DOCUMENTS

| | | | |
|---|---|---|---|
| 4,798,619 | 1/1989 | Los | 71/66 |
| 5,030,271 | 7/1991 | Watkins | 71/92 |
| 5,461,019 | 10/1995 | Willms et al. | 504/130 |
| 5,502,271 | 3/1996 | Donn | 800/200 |
| 5,614,466 | 3/1997 | Boyles et al. | 504/110 |
| 5,696,051 | 12/1997 | Willms et al. | 504/130 |

FOREIGN PATENT DOCUMENTS

| | | |
|---|---|---|
| 2584265 | 4/1986 | France . |

OTHER PUBLICATIONS

Ferreira, et al., Physiological Basis for Antagonism of Fluazifop–P by DPX–PE350, Weed Science, 1995, vol. 43:184–191.

The Agrochemicals Handbook, "Imazapyr".

Dicamba Antagonizes Grass Weed Control with Imazethapyr by Reducing Foliar Absorption, S. E. Hart and L. M. Wax, Weed Technology, 1996, vol. 10:828–834, pp. 828–834.

*Primary Examiner*—S. Mark Clardy
*Attorney, Agent, or Firm*—John W. Hogan, Jr.

[57] ABSTRACT

There is provided a method to overcome or decrease the antagonistic interaction caused by the application of an acetohydroxyacid synthase-inhibiting herbicide in combination with a non-acetohydroxyacid synthase-inhibiting herbicide such as dicamba, 2,4-D, bromoxynil, atrazine or bentazone, which comprises applying an effective amount of imazapyr (2-(4-isopropyl-4-methyl-5-oxo-2-imidazolin-2-yl)nicotinic acid).

20 Claims, No Drawings

METHOD TO OVERCOME THE ANTAGONISTIC INTERACTIONS OF HERBICIDES

This application claims priority from copending provisional application Ser. No. 60/019,562 filed on Jun. 11, 1996.

BACKGROUND OF THE INVENTION

Mankind is dependent upon field crops for food, fiber, animal feed and the like. The ever increasing world population dictates the necessity to produce more from each hectare and, at the same time, to preserve and protect the environment and natural resources that make such production a possibility. Successful crop production and environmental concerns have led professional agriculturalists to implement pest management practices.

Good pest management practices include resistance management practice, i.e. combining herbicides with other herbicides having a different mode of action and combining herbicides with other weed-control techniques. The extensive and continued use of herbicides has lead to important weed resistance problems. Therefore, herbicides of varying modes of action are being used in combinations, applied separately or together, as an integral part of a broad, overall weed-control program tailored to reduce herbicide use rates, enhance the spectrum of weed control, prevent resistant weed species and reduce energy and fuel expenditures.

However, in actual practice, the simultaneous or sequential application of two or more herbicides may result in an undesirable interaction of a biological nature, such as altering the selectivity of the herbicide or decreasing the efficacy of the herbicide. Herbicide interactions are generally categorized as additive, synergistic or antagonistic. The interactions are described as synergistic when the net effect is an enhancement of biological activity and antagonistic when the net effect is a decrease in the biological activity. In other words, an antagonistic interaction of a herbicide combination is a less than additive toxic action of two or more herbicides when used together. Herbicide combination applications which result in an antagonistic interaction are herein described as antagonistic herbicide combinations.

Antagonistic herbicide combinations can increase weed-crop competition and the risk of weeds growing unchecked in periods of adverse weather or soil conditions resulting in reduced crop yields and crop quality and enhanced production and harvest costs.

Therefore, it is an object of this invention to protect vide a method to overcome the antagonistic interaction of herbicide combinations.

It is another object of this invention to provide a method to improve the weed control of antagonistic herbicide combinations used in resistance management practice.

It is a further object of this invention to provide compositions of herbicide combinations useful for improved weed control.

These and other objects and features of the invention will become apparent from the detailed description set forth below.

SUMMARY OF THE INVENTION

There is provided a method to overcome or prevent the antagonistic interaction caused by the application of an acetohydroxyacid synthase-inhibiting (AHAS-inhibiting) herbicide in combination with a non-AHAS-inhibiting herbicide such as dicamba, bromoxynil, 2,4-D, atrazine, bentazone or the like, to undesirable plant species which comprises applying an effective amount of 2-(4-isopropyl-4-methyl-5-oxo-2-imidazolin-2-yl) nicotinic acid to said plant species or the medium in which it is growing or intended to be grown.

Also provided are methods and compositions useful for improved weed control and suitable for inclusion in resistance management practice.

DETAILED DESCRIPTION OF THE INVENTION

With the advent of imidazolinone-resistant and imidazolinone-tolerant crops, the imidazolinone class of herbicides becomes increasingly accessible for use in pest management systems. Because the imidazolinones are highly potent herbicides which are environmentally benign, they are highly suitable for use in herbicide combination applications particularly wherein the tank-mix partner is a herbicide with a different mode of action, i.e., a non-AHAS-inhibiting herbicide. Use of an imidazolinone in said herbicide combination may: (a) signifiber cantly lower the use rate of the tank-mix partner thus decreasing the herbicide load on the environment by as much as 60–90%; (b) enhance the spectrum of weeds effectively controlled; (c) provide an alternate mode of action for improved weed resistance management and (d) allow effective weed control in a single herbicide application resulting in significant savings of fuel, energy and time expenditures.

However, combinations of AHAS-inhibiting herbicides, such as the imidazolinone herbicides, with non-AHAS-inhibiting herbicides such as dicamba, bromoxynil, 2,4-D, atrazine, bentazone and the like may result in an antagonistic interaction. That is, an unexpected loss of weed-control may occur and this loss or reduction of weed-control can be problematic.

Advantageously, it has now been found that the antagonistic interaction resulting from the application of an AHAS-inhibiting herbicide in combination with a non-AHAS-inhibiting herbicide to undesirable or troublesome weeds may be overcome or decreased by the concurrent or sequential application of an effective amount of 2-(4-isopropyl-4-methyl-5-oxo-2-imidazolin-2-yl)nicotinic acid to said weeds.

Said nicotinic acid compound may be applied simultaneously as a tank-mix partner or a co-formulant or sequentially as a separate application either alone or in combination with one or the other of the AHAS-inhibiting herbicide or the non-AHAS-inhibiting herbicide. Preferably, the nicotinic acid compound may be applied as a tank-mix partner or as a co-formulant in a three-part combination application.

The AHAS-inhibiting herbicide may be any herbicide having a mode of action whereby the acetohydroxyacid synthase enzyme is inhibited, for example, imidazolinone herbicides such as imazethapyr, imazameth, imazamox, imazaquin, and the like; sulfonyl urea herbicides such as primisulfuron, nicosulfuron, chlorosulfuron, prosulfuron, halosulfuron, chlorimuron, and the like. AHAS-inhibiting herbicides are also known as acetolactate synthase inhibiting (ALS-inhibiting) herbicides.

The non-AHAS inhibiting herbicide may be any herbicide having a mode of action which does not involve the inhibition of an acetohydroxy acid synthase such as those herbicides which are hormone mimics, photosynthesis inhibitors, protox inhibitors, acetyl-coenzyme A carboxylase inhibitors and the like. Non-AHAS-inhibiting herbicides include, but are not limited to, broadleaved herbicides such as dicamba, 2,4-D, bromoxynil, atrazine, bentazone and the like.

The two herbicidal components of the antagonistic herbicide combination may be present at rates sufficient to induce antagonism. Typically said herbicides are present at a ratio of about 1:1 to 1:10 of AHAS-inhibiting herbicide to non-AHAS-inhibiting herbicide, more typically about 1:3 to 1:5.

The effective amount of 2-(4-isopropyl-4-methyl-5-oxo-2-imidazolin-2-yl)nicotinic acid will vary according to the prevailing conditions such as weather conditions, plant species, weed pressure, stage of growth, mode of application, cultivation practice and the like. Generally, effective amounts of said nicotinic acid may be about 0.008 kg/ha to 0.071 kg/ha, preferably about 0.008 kg/ha to 0.025 kg/ha.

Advantageously, the method of invention may be used to improve weed control at varied sites such as industrial, agricultural, recreational, ornamental and the like. In the instance of agricultural weed control, the method of invention is suitable for use in the presence of crop plant species and particularly in the presence of imidazolinone resistant or tolerant crop species such as IMI-CORN™ maize, IMI™ canola, IMI™ wheat, IMI™ cotton, IMI™ rice and the like.

Concurrent application to undesirable weed species of an antagonistic herbicide combination and an effective amount of 2-(4-isopropyl-4-methyl-5-oxo-2-imidazolin-2-yl) nicotinic acid may be facilitated by a single prepackaged formulation. Therefore, the present invention also provides a composition comprising an AHAS-inhibiting herbicide; a non-AHAS-inhibiting herbicide such as dicamba, 2,4-D, bromoxynil, atrazine, bentazone and the like; 2-(4-isopropyl-4-methyl-5-oxo-2-imidazolin-2-yl)nicotinic acid and an agriculturally acceptable carrier. Generally the ratio of the AHAS-inhibiting herbicide to the non-AHAS inhibiting herbicide will be about 1:1 to 1:10 preferably 1:3 to 1:5 and the ratio of the non-AHAS inhibiting herbicide to the nicotinic acid will be about 5:1 to 50:1, preferably 10:1 to 30:1, most preferably about 15:1. Compositions of the invention may be formulated as a wettable dispersible granular, water soluble granular, suspension concentrate, concentrated emulsion, emulsion concentrate, wettable powder and the like.

The agriculturally acceptable carrier may be a solid or liquid. Suitable solid carriers may be any inert carrier commonly used such as natural and synthetic clays and silicates, natural and synthetic resins, solid fertilizers and the like. Typical examples of a solid carrier include diatomaceous earth, talc, attapulgite, vermiculite, kaolinite, mica, calcium carbonate, calcium sulphate, silicon oxide, coumarone resin, polyvinyl chloride, styrene and the like. Similarly, suitable liquid carriers include water, glycols, alcohols, ketones, ethers, aromatic or araliphatic hydrocarbons, petroleum fractions, and the like, or mixtures thereof.

For a more clear understanding of the invention, specific examples thereof are set forth below. These examples are merely illustrative and are not to be understood as limiting the scope and underlying principles of the invention in any way. Indeed, various modifications of the invention, in addition to those shown and described herein, will become apparent to those skilled in the art from the following examples and foregoing description. Such modifications are also intended to fall within the scope of the appended claims.

EXAMPLE 1

Evaluation Of The Antagonistic Interaction Of Imazethapyr In Combination With Dicamba In these evaluations, small field plots ranging in size from about 3 to 4.4 meters by about 7 to 12 meters are used in a randomized complete block design with 3 to 4 replications. Soil types include sandy loam, silt loam and loam soils. All treatments are applied using standard accepted weed science procedures. Applications are made by tractor or backpack sprayers. All treatments include 0.25% v/v of a nonionic surfactant and 28% v/v of a liquid nitrogen formula. Commercially available formulations of the herbicide are used and the carrier employed is water. All combination herbicide treatments are tank-mixed prior to application. Test applications are made about 26 to 32 days after planting, when the IMI-CORN™ crop is in the 2 to 6 leaf stage and the weeds are approximately 2.5 to 18 cm in height. Evaluations are made periodically and recorded as % weed control. In these tests, no injury to the IMI-CORN™ maize crop is observed. The results at 56 days after treatment (DAT) are shown in Table I.

| WEED SPECIES | | |
|---|---|---|
| Code | Scientific Name | Common Name |
| DIGSA | Digitaria sanguinalis (L.) | Crabgrass, large |
| ECHSS | Echinochloa P. BEAUV. | Barnyardgrass |
| PANDI | Panicum dichotomiflorum (L.) | Panicum, Fall |
| SETVI | Setaria viridis (L.) P. BEAUV. | Foxtail, green |
| SETFA | Setaria faberi HERRM. | Foxtail, giant |

| COMMERCIAL HERBICIDES | |
|---|---|
| Herbicide | Tradename |
| Imazethapyr | PURSUIT ®, American Cyanamid Co. |
| Dicamba | BANVEL ®, Sandoz |

TABLE I

| AHAS Herbicide | Rate kg/ha | Rate (kg/ha) Dicamba | % Weed Control | | | | |
|---|---|---|---|---|---|---|---|
| | | | DIGSA | ECHSS | PANDI | SETVI | SETFA |
| Imazethapyr | 0.036 | 0 | 70 | 73 | 62 | 45 | 67 |
| Imazethapyr | 0.053 | 0 | 73 | 33 | 82 | 100 | 76 |
| Imazethapyr | 0.071 | 0 | 87 | 30 | 87 | 93 | 83 |
| Imazethapyr | 0.036 | 0.071 | — | 20 | — | — | — |
| Imazethapyr | 0.036 | 0.140 | 43 | 0 | 25 | 75 | 66 |
| Imazethapyr | 0.036 | 0.211 | — | 0 | — | — | — |
| Imazethapyr | 0.036 | 0.280 | 47 | 0 | 20 | 65 | 61 |
| Imazethapyr | 0.036 | 0.560 | 57 | — | 15 | 57 | 48 |
| Imazethapyr | 0.053 | 0.140 | 65 | 13 | — | 87 | 68 |
| Imazethapyr | 0.053 | 0.211 | — | 0 | — | — | — |
| Imazethapyr | 0.053 | 0.280 | 58 | 7 | 48 | 60 | 56 |
| Imazethapyr | 0.053 | 0.560 | 57 | — | 37 | 67 | 59 |

TABLE I-continued

| AHAS Herbicide | Rate kg/ha | Rate (kg/ha) Dicamba | % Weed Control | | | |
|---|---|---|---|---|---|---|
| | | | DIGSA | ECHSS | PANDI | SETVI | SETFA |
| Imazethapyr | 0.071 | 0.140 | 60 | 10 | 63 | 57 | 68 |
| Imazethapyr | 0.071 | 0.211 | — | 17 | — | — | — |
| Imazethapyr | 0.071 | 0.280 | 60 | 15 | 50 | 73 | 73 |

EXAMPLE 2
Evaluation Of The Antagonistic Interaction Of Imazethapyr In Combination With Bromoxynil Using essentially the same procedure described in Example 1 but employing bromoxynil as one of the commercially available herbicides and varying the geographic location of the test site, the following results are obtained and shown in Table II. In this evaluation, no injury to the IMI-CORN™ maize crop is observed.

| WEED SPECIES | | |
|---|---|---|
| Code | Scientific Name | Common Name |
| ECHSS | Echinochloa P. BEAUV. | Barnyardgrass |
| SETFA | Setaria faberi HERRM. | Foxtail, giant |
| DIGSA | Digitaria sanguinalis (L.) | Crabgrass, large |

| COMMERCIAL HERBICIDES | |
|---|---|
| Herbicide | Tradename |
| Imazethapyr | PURSUIT ®, American Cyanamid Co. |
| Bromoxynil | BUCTRIL ®, Rhône Poulenc | shown in Table III. In this evaluation, no injury to the IMI-CORN™ maize crop is observed. The weed control data shown on Table III is obtained at 28 days after treatment.

| WEED SPECIES | | |
|---|---|---|
| Code | Scientific Name | Common Name |
| ECHSS | Echinochloa P. BEAUV. | Barnyardgrass |
| ERBVI | Eriochloa villosa (THUNB.) | Cupgrass, woody |
| PANDI | Panicum dichotomiflorum (L.) | Panicum, fall |
| SETFA | Setaria faberi HERRM. | Foxtail, giant |
| SORHA | Sorghum halapense (L.) PERS. | Johnsongrass |

| COMMERCIAL HERBICIDES | |
|---|---|
| Herbicide | Tradename |
| Imazethapyr | PURSUIT ®, American Cyanamid Co. |
| Dicamba | BANVEL ®, Sandoz |
| Imazapyr* | ARSENAL ®, American Cyanamid Co. |

*2-(4-isopropyl-4-methyl-5-oxo-2-imidazolin-2-yl)nicotinic acid

TABLE II

| AHAS Herbicide | Rate kg/ha | Rate (kg/ha) Bromoxynil | % Weed Control | | | | |
|---|---|---|---|---|---|---|---|
| | | | ECHSS 42 DAT | SETFA 14 DAT | DIGSA 14 DAT | DIGSA 28 DAT | DIGSA 56 DAT |
| Imazethapyr | 0.071 | 0 | 75 | 85 | 97 | 94 | 87 |
| Imazethapyr | 0.071 | 0.140 | 71 | 78 | 95 | 95 | 73 |
| Imazethapyr | 0.071 | 0.280 | 64 | 81 | 90 | 90 | 73 |

EXAMPLE 3
Evaluation Of The Effect Of 2-(4-Isopropyl-4-methyl-5-oxo-2-imidazolin-2-yl)nicotinic acid On The Antagonistic Interaction Of Imazethapyr In Combination With Dicamba Using essentially the same procedure described in Example 1 and adding 2-(4-isopropyl-4-methyl-5-oxo-2-imidazolin -2-yl) nicotinic acid to the combination of commercial herbicides, the following results are obtained and

TABLE III

| AHAS Herbicide | Rate kg/ha | Rate (kg/ha) | | % Weed Control | | | | |
|---|---|---|---|---|---|---|---|---|
| | | Dicamba | Imazapyr | ECHSS | ERBVE | PANDI | SETFA | SORHA |
| Imazethapyr | 0.071 | 0 | 0 | 77 | 68 | 81 | 81 | 93 |
| Imazethapyr | 0.071 | 0.168 | 0 | 47 | 46 | 81 | 69 | 89 |
| Imazethapyr | 0.071 | 0.211 | 0 | 53 | 67 | 75 | 69 | 76 |
| Imazethapyr | 0.047 | 0.168 | 0.016 | 93 | 91 | 93 | 94 | 99 |
| Imazethapyr | 0.047 | 0.211 | 0.016 | 92 | 92 | 92 | 90 | 98 |

EXAMPLE 4
Evaluation Of The Effect Of 2-(4-Isopropyl-4-methyl-5-oxo-2-imidazolin-2-yl) nicotinic acid On The Antagonistic Of Interaction Of Imazethapyr In Combination With Bromoxynil Using essentially the same procedure described in Example 2 and adding 2-(4-isopropyl-4-methyl-5-oxo-2-imidazolin-2-yl) nicotinic acid to the combination of commercial herbicides, the following results are obtained and shown in Table IV.

In this evaluation, no injury to the IMI-CORN™ maize crop is observed. The weed control data shown on Table IV is obtained at 56 days after treatment.

| WEED SPECIES | | |
|---|---|---|
| Code | Scientific Name | Common Name |
| ECHSS | Echinochloa P. BEAUV. | Barnyardgrass |
| SETFA | *Setaria faberi* HERRM. | Foxtail, giant |
| SETVI | *Setaria viridis* (L.) P. BEAUV. | Foxtail green |
| DIGSA | *Digitaria sanguinalis* (L.) | Crabgrass, large |

| COMMERCIAL HERBICIDES | |
|---|---|
| Herbicide | Tradename |
| Imazethapyr | PURSUIT ®, American Cyanamid Co. |
| Bromoxynil | BUCTRIL ®, Rhône Poulenc |
| Imazapyr* | ARSENAL ®, American Cyanamid Co. |

*2-(4-isopropyl-4-methyl-5-oxo-2-imidazolin-2-yl)nicotinic acid

TABLE IV

| AHAS Herbicide | Rate kg/ha | Rate (kg/ha) Bromoxynil | Imazapyr | % Weed Control ECHSS | SETFA | SETVI | DIGSA |
|---|---|---|---|---|---|---|---|
| Imazethapyr | 0.071 | 0 | 0 | 87 | 65 | 90 | 88 |
| Imazethapyr | 0.071 | 0.168 | 0 | 77 | 85 | 43 | 47 |
| Imazethapyr | 0.047 | 0.168 | 0.016 | 90 | 89 | 85 | 87 |

What is claimed is:

1. A method for the improved control of undesirable plant species which comprises applying to said plant species
   a) an acetohydroxy acid synthase-inhibiting herbicide,
   b) a non-acethohydroxy acid synthase-inhibiting herbicide, and
   c) 2-(4-ispropyl-4-methyl-5-oxo-2-imidazolin-2-yl) nicotinic acid
   wherein component a and component b are applied at rates which if applied without component c would be antagonistic and wherein component c is applied at an effective rate and timing such that it overcomes or reduces the antagonistic interaction of components a and b, said timing of application of component c being simultaneous with component a and b, or sequential as a separate application either alone or in combination with one or the other of component a or b.

2. The method according to claim 1 wherein the non-acetohydroxy acid synthase-inhibiting herbicide is selected from the group consisting of a photosynthesis-inhibitor, a hormone mimic, a protox inhibitor, and an acetyl-coenzyme A carboxylase inhibitor.

3. The method according to claim 2 wherein the non-acetohydroxy acid synthase-inhibiting herbicide is selected from the group consisting of dicamba, 2,4-D, bromoxynil, atrazine and bentazone.

4. The method according to claim 3 wherein the non-acetohydroxy acid synthase-inhibiting herbicide is dicamba, 2,4-D or bromoxynil.

5. The method according to claim 1 wherein the acetohydroxy acid synthase-inhibiting herbicide is an imidazolinone herbicide.

6. The method according to claim 5 wherein the imidazolinone herbicide is selected from the group consisting of imazethapyr, imazameth, imazaquin and imazamox.

7. The method according to claim 6 wherein the imidazolinone herbicide is imazethapyr.

8. The method according to claim 7 wherein component c is applied simultaneously with said imazethapyr.

9. The method according to claim 7 wherein the imazethapyr herbicide and the non-acetohydroxy acid synthase-inhibiting herbicide are present in a ratio of about 1:1 to 1:10.

10. The method according to claim 9 wherein the non-acetohydroxy acid synthase-inhibiting herbicide is selected from the group consisting of dicamba, 2,4-D, bromoxynil, atrazine and bentazone.

11. The method according to claim 10 wherein the ratio of the non-acetohydroxy acid synthase-inhibiting herbicide to the 2-(4-ispropyl-4-methyl-5-oxo-2-imidazolin-2-yl) nicotinic acid is about 5:1 to 50:1.

12. The method according to claim 11 wherein the non-acetohydroxy acid synthase-inhibiting herbicide is dicamba.

13. The method according to claim 1 wherein the undesirable plant species are monocotyledonous plant species.

14. The method according to claim 1 wherein the undesirable plant species are growing in the presence of a crop.

15. The method according to claim 14 wherein the crop is maize.

16. The method according to claim 15 wherein the maize is imidazolinone resistant or imidazolinone tolerant maize.

17. The method according to claim 1 wherein the 2-(4-isopropyl-4-methyl-5-oxo-2-imidazolin-2-yl)nicotinic acid is applied at a rate of about 0.008 kg/ha to 0.071 kg/ha.

18. The method according to claim 1 wherein components a, b, and c are applied simultaneously.

19. A composition which comprises
   a) an acetohydroxy acid synthase-inhibiting herbicide,
   b) a non-acetohydroxy acid synthase-inhibiting herbicide,
   c) 2-(4-isopropyl-4-methyl-5-oxo-2-imidazolin-2-yl) nicotinic acid and
   d) an agriculturally acceptable carrier.

20. The composition according to claim 19 wherein acetohydroxy acid synthase-inhibiting herbicide is imazethapyr and the non-acetohydroxy acid synthase-inhibiting herbicide is selected from the group consisting of dicamba, 2,4-D, bromoxynil, atrazine and bentazone.

* * * * *